United States Patent [19]
Yao et al.

[11] Patent Number: 5,733,120
[45] Date of Patent: Mar. 31, 1998

[54] DENTAL HANDPIECE CAPABLE OF STABLE SUPPORTING TURBINE

[75] Inventors: Atsushi Yao, Kashihara; Masahiro Mukasa, Nara, both of Japan

[73] Assignee: Koyo Seiko Co., Ltd., Osaka, Japan

[21] Appl. No.: 561,243

[22] Filed: Nov. 21, 1995

[30] Foreign Application Priority Data

Nov. 25, 1994 [JP] Japan ................... 6-291769

[51] Int. Cl.$^6$ ................................................ A61C 1/05
[52] U.S. Cl. ............................................... 433/132
[58] Field of Search ........................ 433/114, 117, 433/126, 131, 132

[56] References Cited

U.S. PATENT DOCUMENTS

| | | | |
|---|---|---|---|
| 2,945,299 | 7/1960 | Fritz | 433/126 |
| 3,132,426 | 5/1964 | White | 433/132 |
| 4,071,954 | 2/1978 | Eibofner | 433/132 |
| 4,120,623 | 10/1978 | Lohn | 433/132 |
| 4,146,964 | 4/1979 | Lares et al. | 433/132 |
| 4,219,330 | 8/1980 | Jaremus | 433/132 |
| 4,249,896 | 2/1981 | Kerfoot, Jr. | 433/132 |
| 4,533,324 | 8/1985 | Nakanishi | 433/132 |
| 5,252,067 | 10/1993 | Kakimoto | |
| 5,308,242 | 5/1994 | McLaughlin et al. | |
| 5,334,013 | 8/1994 | Meller | 433/132 |
| 5,336,089 | 8/1994 | Sakurai | |
| 5,507,642 | 4/1996 | Wohlgemuth | 433/132 |

FOREIGN PATENT DOCUMENTS

| | | | |
|---|---|---|---|
| 260865 | 10/1988 | Germany | 433/126 |
| 610944 | 10/1960 | Italy | 433/132 |

*Primary Examiner*—Ralph Lewis
*Attorney, Agent, or Firm*—Wenderoth, Lind & Ponack

[57] ABSTRACT

There is provided a dental handpiece capable of stably supporting a turbine during high-speed rotation thereof. A projection is provided at each corner portion of a polygonal end surface of a retainer. The projections prevent a conical spring washer from deviating from a centered position relative to the central axis of the turbine. First and second ball bearings for supporting the turbine are axially pressed with a sufficient force which is symmetrical about the central axis of the turbine. A sufficient axial pre-load can be applied to the first and second ball bearings by the conical spring washer, and the conical spring washer is prevented from being displaced.

5 Claims, 5 Drawing Sheets

DENTAL HANDPIECE CAPABLE OF STABLE SUPPORTING TURBINE

BACKGROUND OF THE INVENTION

1. Field of the Invention

The present invention relates to a dental handpiece having a turbine for rotating, at high speeds, a cutting tool for cutting a tooth.

2. Description of the Prior Art

A conventional dental handpiece of the above-mentioned type is shown in FIG. 7. The dental handpiece is made of a metal and is connected to an air power source (not shown). The handpiece has a turbine 62 provided inside a housing 61. The turbine 62 has shaft portions 65a and 65b which are fit in two ball bearings 63 and 64, and an impeller portion 66 provided between the shaft portions 65a and 65b. The shaft portions 65a and 65b and the impeller portion 66 are made of a resin and are integrally formed. Further, a cutting tool can be mounted on the shaft portion 65b. Air for rotating the impeller portion 66 flows into and out of a shank portion 61a of the housing 61.

A retainer 68 is closely fit on the ball bearing 63. The retainer 68 has a sectionally-polygonal outer circumferential surface, and the sectionally-polygonal outer circumferential surface is clearance fit in a sectionally-polygonal inner circumferential surface of the housing 61. Since the retainer 68 and the housing 61 are thus fit to each other on their sectionally-polygonal surfaces, the retainer 68 does not rotate relative to the housing 61. Therefore, an outer ring of the ball bearing 63 does not rotate with the turbine 62 when the turbine 62 rotates.

The retainer 68 has a flange portion 68a which faces an end surface of the outer ring of the ball bearing 63, and the flange portion 68a is axially pressed by a lid 67 so that it axially presses the ball bearing 63 against the impeller portion 66. The lid 67 is fit in a space between an axial end portion 65a-1 of the shaft portion 65a and the housing 61 opposite to the axial end portion 65a-1.

In the above-mentioned dental handpiece, the impeller portion 66 is rotated by air flowing from the shank portion 61a, and the shaft portions 65a and 65b rotate with the impeller portion. Then, the air which has rotated the impeller portion 66 returns to the inside of the shank portion 61a and then flows out of the shank portion 61a.

In the above-mentioned dental handpiece, shield plates 69a and 69b are provided respectively at an end portion of a ball bearing 64 on the impeller portion 66 side and at an end portion of the impeller portion 66 on the ball bearing 63, so that air does not flow out of the ball bearings 63 and 64.

However, in the above-mentioned prior art dental handpiece, the lid 67 does not have a sufficient force to press the retainer 68, and accordingly, a force is not obtained which is sufficient to axially press the ball bearing 63. The above fact causes a problem in that the turbine 62 will shake in the axial direction when the rotating speed of the impeller portion 66 is high.

In view of the above, a conical spring washer (not shown) is provided between the lid 67 and the retainer 68 so as to axially press the retainer by the conical spring washer. However, in this case, there is the problem that an edge portion of the conical spring washer can slide toward a corner portion of the sectionally-polygonal inner circumferential surface of the housing, thereby displacing the conical spring washer. In this case, the force to axially press the ball bearing deviates to the center axis, and therefore the turbine cannot be stably supported.

SUMMARY OF THE INVENTION

The object of the present invention is therefore to provide a dental handpiece capable of applying a sufficient axial pre-load to ball bearings by means of a conical spring washer while preventing the displacement of the conical spring washer.

In order to achieve the aforementioned object, the present invention provides a dental handpiece having a housing made of a synthetic resin and including a shank portion adapted to conduct air flow in and out. A turbine, which is made of a synthetic resin, is arranged inside the housing and has an integral impeller portion to which air from the shank portion is supplied. First and second shaft portions extend axially from the impeller portion toward opposite sides of the housing. First and second ball bearings are arranged between the first shaft portion of the turbine and the housing and between the second shaft portion and the housing, and are fit to the first and second shaft portions, respectively. The dental handpiece further includes a retainer, a lid, and a conical spring washer biasing the retainer toward the impeller.

According to the present invention, a formation provided on the end surface of the retainer or the inner circumferential surface of the housing radially supports the conical spring washer. Thus, the conical spring washer does not displace toward the corner portion. That is to say, the position of the conical spring washer does not deviate from the central axis of the retainer. Therefore, the conical spring washer axially presses the retainer with a force which is symmetrical about the central axis of the retainer. Consequently, the turbine is prevented from shaking along an axial direction even when the rotating speed of the turbine is increased, thereby allowing the turbine to be stably supported during high-speed rotation.

In an embodiment, the inner circumferential surface of the housing and the outer circumferential surface of the retainer have polygonal sectional shapes which are circumferentially engaged with each other. The formation for radially supporting the conical spring washer comprises projections formed at respective corner portions on the end surface of the polygonal sectional shape of the retainer.

According to the embodiment, the sectionally-polygonal inner circumferential surface of the housing and the sectionally-polygonal outer circumferential surface of the retainer are engaged with each other. Thus, the retainer is prevented from rotating relative to the housing. Also, the projections at the respective corners of the sectionally-polygonal end surface of the retainer radially support the conical spring washer. Thus, the conical spring washer does not deviate from the central axis of the retainer. Therefore, the conical spring washer axially presses the retainer with a force which is symmetrical about the central axis of the retainer. Accordingly, the turbine is prevented from shaking along the axial direction.

In an embodiment, each of the projections is so shaped as to have a surface which is inclined relative to the end surface of the retainer, and has an amount of protrusion that increases as the radial distance measured away from the center of the end surface increases.

With the above arrangement, the conical spring washer is easily guided in its normal position by the inclined surfaces of the projections.

In an embodiment, the inner circumferential surface of the housing and the outer circumferential surface of the retainer are cylindrical surfaces to be fit with each other, the inner circumferential surface of the housing and the outer circumferential surface of the retainer have engagement portions which are circumferentially engaged with each other, and the formation for radially supporting the conical spring washer is the cylindrical surface of the housing.

With the above-mentioned arrangement, the engagement portions of the housing and the retainer are engaged with each other, thereby preventing the retainer from rotating relative to the housing. Also, the conical spring washer is easily prevented from deviating from the central axis of the retainer, because the conical spring washer is radially supported by the cylindrical surface of the housing. Accordingly, the turbine is prevented from shaking along an axial direction.

In an embodiment, a groove for allowing air to pass is formed in at least one of an outer circumferential surface of the outer ring of the first ball bearing, an outer circumferential surface of an outer ring of the second ball bearing, an inner circumferential surface of an inner ring of the first ball bearing, an inner circumferential surface of an inner ring of the second ball bearing, the inner circumferential surface of the housing fit to the outer circumferential surface of the retainer, and an inner circumferential surface of the housing fit to the outer ring of the second ball bearing.

According to the above-mentioned embodiment, the air is partially discharged outwardly from inside the housing through the groove. Therefore, dust and any foreign matter are prevented from entering from the outside to the inside of the housing. Furthermore, the ball bearing is sealed, and therefore the possible scattering of lubricant oil from inside the ball bearing is prevented.

According to the dental handpiece of a further embodiment, the projections for radially supporting the conical spring washer are formed at respective corner portions of the polygonal end surface of the retainer which is pressed by the conical spring washer. Thus, the conical spring washer does not displace toward the corner portions.

According to the dental handpiece of the present embodiment, the cylindrical inner circumferential surface of the housing has a convexity or a convex portion which protrudes radially and extends axially or a concavity or concave portion which is radially recessed and extends axially. The retainer is provided with the cylindrical outer circumferential surface having the concave portion or the convex portion to be fit to the convex portion or the concave portion of the housing.

Therefore, according to the present embodiment, possible relative rotation of the housing and the retainer is prevented by making the convex and concave portions formed on the respective cylindrical surfaces which engage with each other without using the sectionally-polygonal circumferential surfaces. Furthermore, the conical spring washer which is arranged between the first shaft portion of the turbine and the cylindrical inner circumferential surface of the housing and presses the retainer to the impeller portion is guided on the cylindrical inner circumferential surface of the housing. Therefore, according to the present embodiment, the retainer is axially pressed with sufficient force without causing deviation of the conical spring washer. Therefore, the first and second ball bearings are axially pressed with a sufficient force which is symmetrical about the central axis of the turbine. Accordingly, the turbine is prevented from shaking in the axial direction even when the rotating speed of the turbine is increased, thereby allowing the turbine to be stably supported during high-speed rotation.

BRIEF DESCRIPTION OF THE DRAWINGS

The present invention will become more fully understood from the following detailed description and the accompanying drawings which are given by way of illustration only, and thus do not limit the scope of the present invention.

DETAILED DESCRIPTION OF THE PREFERRED EMBODIMENTS

The present invention will be described in detail below based on embodiments thereof with reference to the accompanying drawings.

Figure 1:
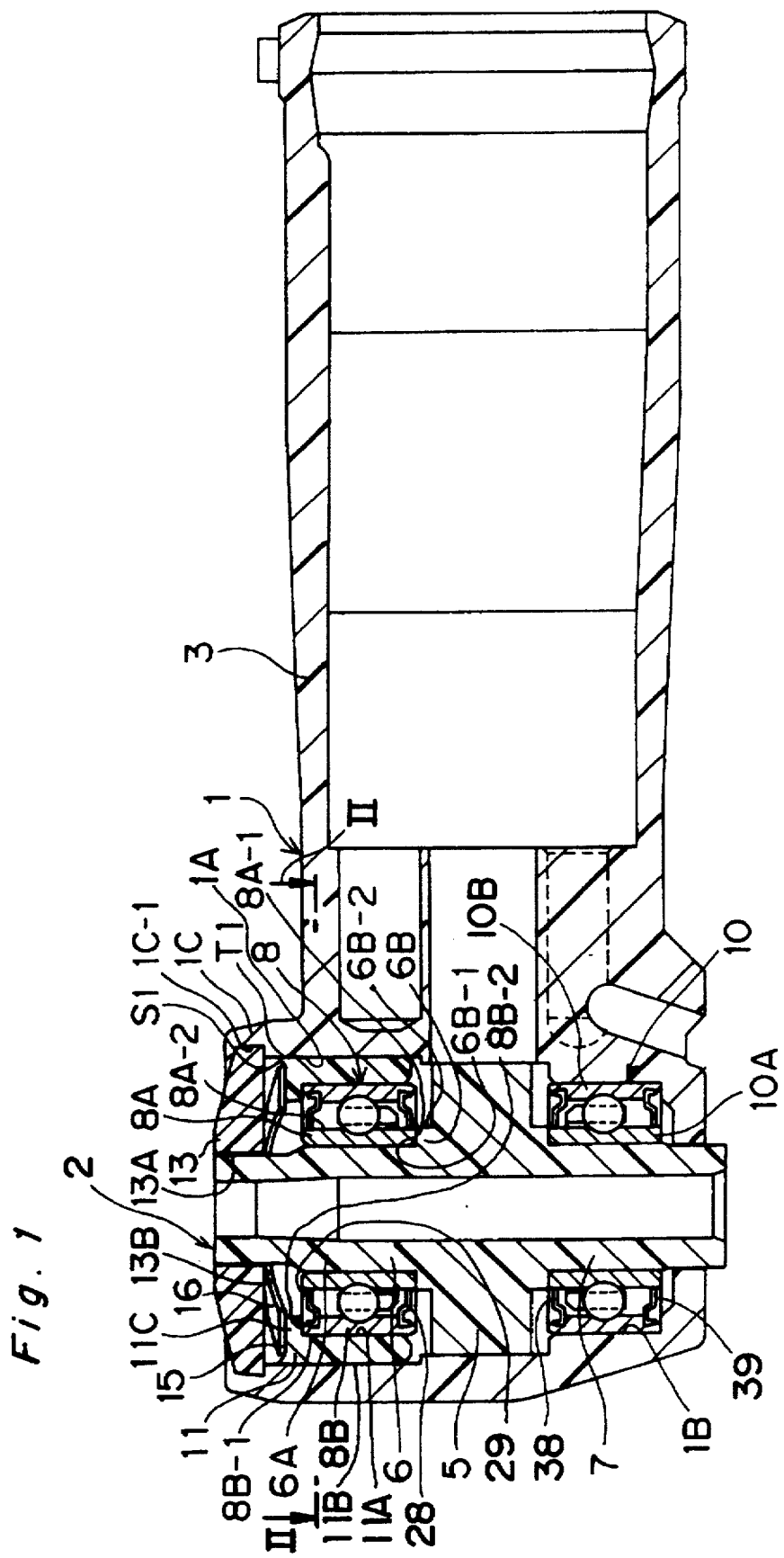
FIG. 1 is a sectional view of a dental handpiece according to a first embodiment of the present invention.

FIG. 1 shows a dental handpiece according to a first embodiment of the present invention. The first embodiment includes a housing 1, made of a synthetic resin such as polypropylene and a turbine 2 which is made of a synthetic resin such as polyacetal and is arranged inside a head portion or section of the housing 1 and has a central hollow portion. The housing 1 has a shank portion 3 where air flows in and out. The turbine 2 has an impeller portion 5 made of a synthetic resin, and first and second shaft portions 6 and 7 which are arranged axially on both sides of the impeller portion 5. A rotary drill such as a cutting tool or the like can be mounted to the hollow portion of the turbine 2. The hollow portion corresponding to the first shaft portion 6 is tapered to a small-diameter portion 6A, so that the drill is effectively supported and held.

An inner ring 8A of a first ball bearing 8 is close fit or interference fit on the outer circumferential surface of the small-diameter portion 6A of the first shaft portion 6. The first shaft portion 6 has a large-diameter portion 6B on the impeller portion 5 side. An end surface 8A-1 of an inner ring 8A of the first ball bearing 8 on the impeller portion 5 side is made to abut an end surface 6B-1 of the large-diameter portion 6B. Further, an outer circumferential surface 6B-2 of the large-diameter portion 6B is made to have the same diameter as that of an outer circumferential surface 8A-2 of the inner ring 8A. Therefore, air from the impeller portion 5 easily flows in the axial direction of the housing, so that the flow of air is smooth and the air flows to some extent inside the ball bearings 8 and 10 and flows outwardly through clearances between the first shaft portion 6 of the turbine 2 and a lid 13, and between the housing 1 and the second shaft portion 7 of the turbine 2. Therefore, a negative internal pressure does not develop in the housing 1 when the impeller portion 5 starts or stops, so that dust and any foreign matter can be effectively prevented from entering from outside the housing.

Figure 2:
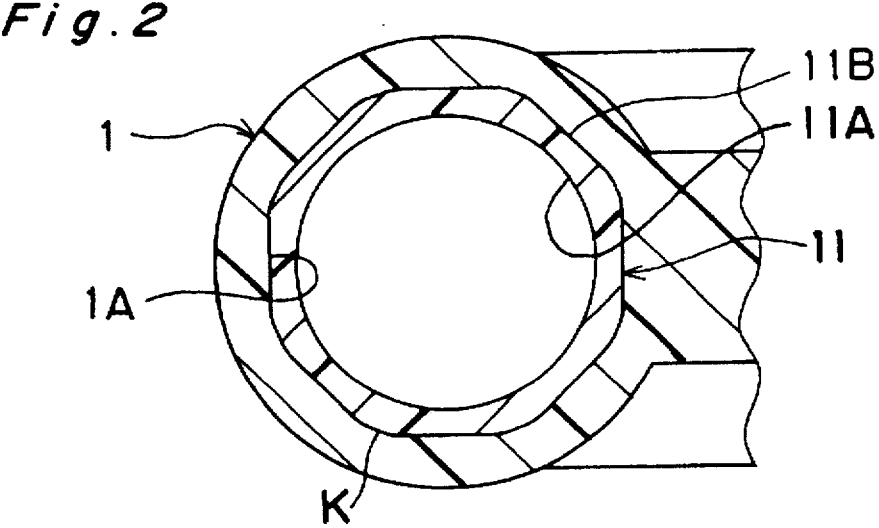
FIG. 2 is a sectional view taken along a line II—II shown in FIG. 1.

An outer circumferential surface 8B-1 of an outer ring 8B of the first ball bearing 8 is interference fit on a cylindrical inner circumferential surface 11A of a retainer 11. Then, as shown in FIG. 2, an outer circumferential surface 11B of the retainer 11 has a sectionally-polygonal cylindrical configuration having an approximately regular octagonal sectional shape. Then, the sectionally-polygonal cylindrical outer circumferential surface 11B having an approximately regular octagonal sectional shape of the retainer 11 is clearance fit in a sectionally-polygonal cylindrical inner circumferential surface 1A having an approximately regular octagonal sectional shape of the housing 1 opposite to the outer circumferential surface 11B. Further, as shown in FIG. 1, the retainer 11 has an inner flange 11C which abuts an axial end surface 8B-2 of the outer ring 8B. As shown in FIG. 2, the housing 1 and the retainer 11 are fit to each other with the inner circumferential surface 1A having an approximately regular octagonal sectional shape and the outer circumferential surface 11B having an approximately regular octagonal sectional shape, and therefore they do not rotate relatively to each other. Further, the retainer 11 and the outer ring 8B of the first ball bearing 8 are closely fit to each other. Therefore, the outer ring 8B of the first ball bearing 8 does not rotate when the turbine 2 rotates.

Meanwhile, an inner ring 10A of a second ball bearing 10 is interference fit on the outer circumferential surface of the second shaft portion 7. Further, an outer circumferential surface of an outer ring 10B of the second ball bearing 10 is interference fit on a cylindrical inner circumferential surface 1B of the housing 1. Even though the outer ring 10B is interference fit on the inner circumferential surface 1B of the housing 1, since the housing 1 made of a synthetic resin has a certain elasticity in comparison with metal, there is no such possibility that the fitting of the second ball bearing 10 may incur blockage. The co-rotation of the outer ring 10B is effectively prevented.

On the inner circumferential surface side of an axial end portion 1C of the housing 1 opposite to the first shaft portion 6 is formed with an annular groove 1C-1, and the lid 13, made of a synthetic resin such as polypropylene, is fit to the annular groove 1C-1. The end portion 6A of the first shaft portion 6 is rotatably fit in a center hole 13A of the lid 13. Then a conical spring washer 16 conforming to JIS SUS304 is provided between an inner surface 13B of the lid 13 and an end surface 15 of the retainer 11. The conical spring washer 16 is pressed by the lid 13 to axially press the end surface 15 of the retainer 11 and then axially press the retainer 11 toward the impeller portion 5. Further, as shown in FIG. 2, the end surface 15 of the retainer 11 has an approximately regular octagonal sectional shape, and, as shown in FIGS. 1 and 2, a projection T1, having an approximately right-angled triangular section having an inclined surface S1 which slopes upward towards the periphery in the direction of the diameter, is formed at each of eight corner portions K of the end surface 15. That is to say, the inclined surfaces S1 are inclined relative to the end surface 15, and have an amount of protrusion that becomes larger with an increase of a distance measured from the center of the end surface 15 and along the end surface 15. Since the projection T1 is formed at the corner portions K, radial movement of the conical spring washer 16 is checked by the projection T1. Further, by the inclined surface S1 which slopes upward towards the periphery in the direction of diameter, the conical spring washer 16 is easily guided to an axial center. Therefore, the conical spring washer 16 is not displaced with respect to the central axis of the turbine 2. Therefore, the conical spring washer 16 presses the end surface 15 of the retainer 11 with force which is symmetrical about the central axis of the turbine 2. Therefore, the inner flange 11C of the retainer 11 presses the end surface 8B-2 of the outer ring 8B of the first ball bearing 8 with a sufficient force which is symmetrical about the central axis. Thus, the inner ring 8A of the first ball bearing 8 axially presses the stepped portion 6B of the turbine 2 with a sufficient force which is symmetrical about the central axis. Consequently, even when the turbine 2 is rotated at high speeds, the turbine 2 can be prevented from shaking in the axial direction. It is to be noted that a paraffin based lubricant oil (trade name: Synfluid 6 cst, produced by Chevron Chemical Co.) having less toxicity is provided between bearing shields 28, 29, 38 and 39 and inside the first and second ball bearings 8 and 10.

In the dental handpiece having the above-mentioned construction, the impeller portion 5 of the turbine 2 is rotated by air flowing in from the shank portion 3 of the housing 1, and consequently, a cutting tool (not shown) mounted to the shaft portion 7 of the turbine 2 is rotated. The turbine 2 is supported axially and radially in the housing 1 by the first and second ball bearings 8 and 10 which are fit on the first and second shaft portions 6 and 7.

As described above, the stepped portion 6B of the first shaft portion 6 of the turbine 2 is pressed axially toward the impeller portion 5 by the conical spring washer 16 via the retainer 11, the outer ring 8B and the inner ring 8A of the first ball bearing 8. Therefore, even when the turbine 2 rotates at high speeds, the turbine 2 does not shake along the axial direction. Furthermore, by virtue of the projection T1 formed at each corner portion K on the end surface 15 of the retainer 11, the conical spring washer 16 is prevented from being displaced radially relative to the central axis of the turbine 2. Therefore, the first ball bearing 8 can be pressed along the axial direction with force which is symmetrical about the central axis. Therefore, the turbine 2 can be always stably supported by the first and second ball bearings 8 and 10. That is, according to the first embodiment, even when the turbine 2 rotates at high speeds, the turbine 2 can always be stably supported by the first and second ball bearings 8 and 10.

Figure 4:
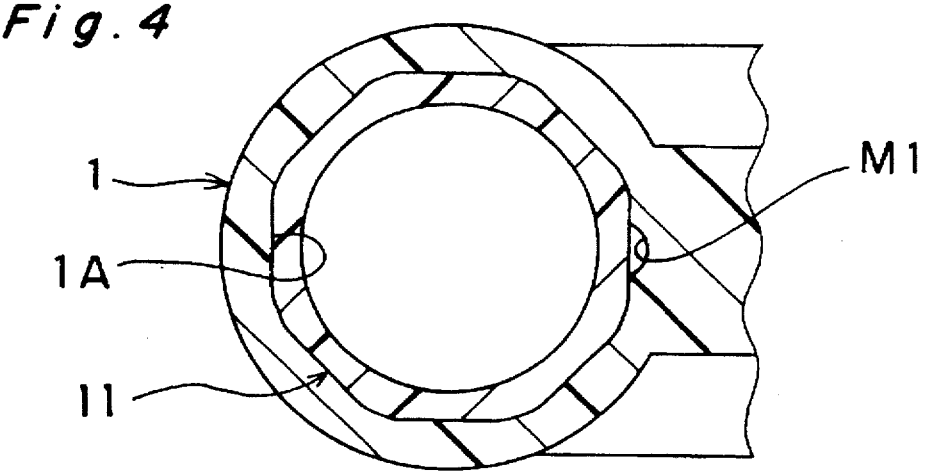
FIG. 4 is a sectional view taken along a line IV—IV shown in FIG. 3.
Figure 3:
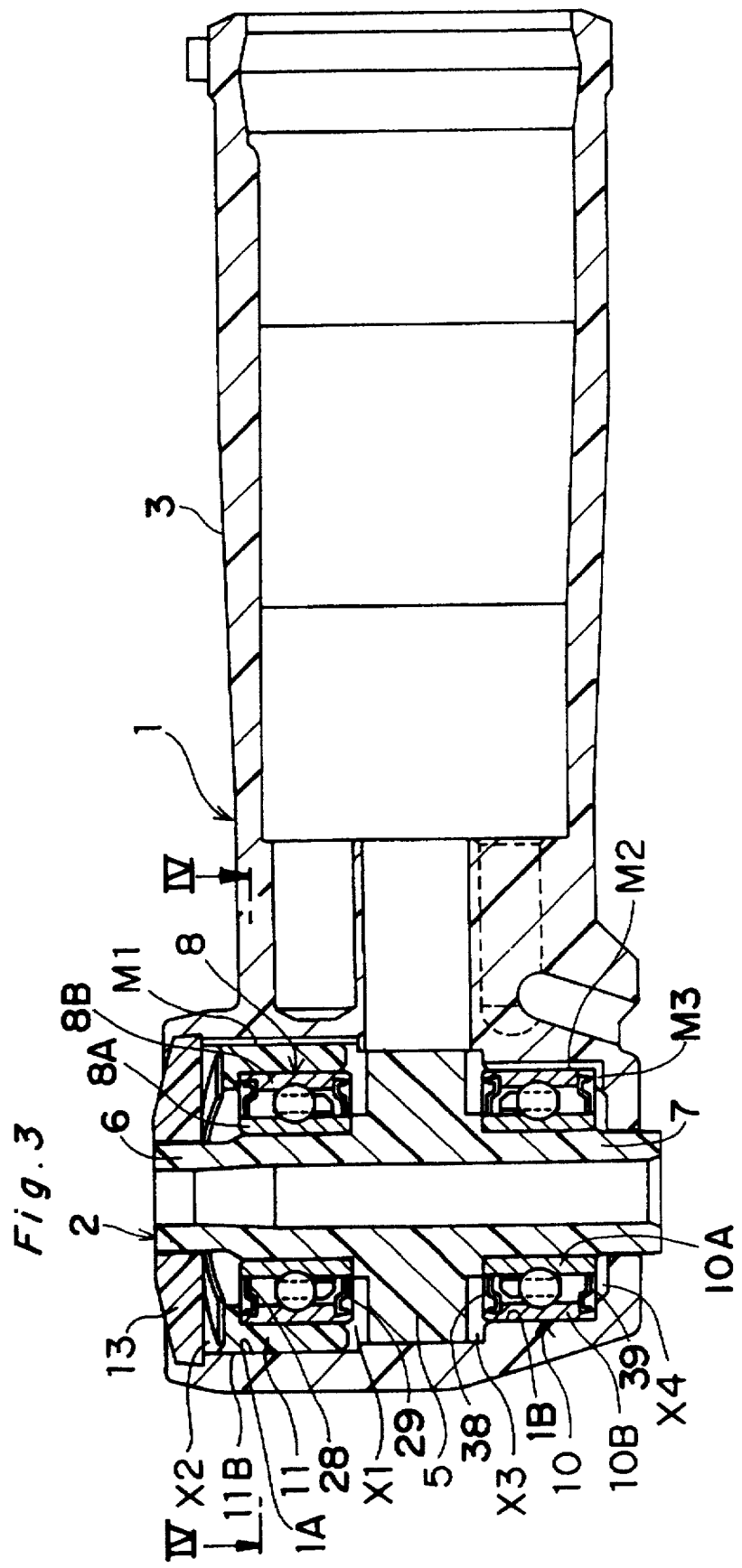
FIG. 3 is a sectional view of a dental handpiece according to a second embodiment of the present invention.

Next, FIGS. 3 and 4 show a dental handpiece according to a second embodiment of the present invention. The second embodiment differs from the first embodiment only in that an air blowoff groove M1 opposite to the outer circumferential surface 11B of a retainer 11 and an air blowoff groove M2 opposite to the outer ring 10B of the second ball bearing 10 are formed in an inner circumferential surface 1B of the housing 1. Also, an air blowoff groove M3 opposite to an end surface of the outer ring 10B of the second ball bearing 10 is formed on an inner end surface of the housing 1 of the dental handpiece. The same components as those of the first embodiment are denoted by the same reference numerals, and no description is provided therefor.

The air blowoff groove M1 extends axially, and has a semicircular sectional shape as shown in FIG. 4. The air blowoff groove M1 establishes communication between a space X1, between the first ball bearing 8 and the impeller portion 5, and a space X2 between the lid 13 and the retainer 11.

The air blowoff groove M2 extends axially, and has a semicircular sectional shape. The air blowoff groove M3 extends radially. The air blowoff grooves M2 and M3 establish communication between a space X3, between the second ball bearing 10 and the impeller portion 5, and a space X4 located axially outside the second ball bearing 10.

According to the second embodiment, part of the air which has rotated the impeller portion 5 can be guided to the outside of the first and second ball bearings 8 and 10 by way of the air blowoff grooves M1, M2 and M3. Then, the air guided to the outside of the ball bearing 8 is discharged outwardly from a gap (not shown) between the lid 13 and the first shaft portion 6 of the turbine 2. Furthermore, the air guided to the outside of the second ball bearing 10 is discharged from a gap (not shown) between the housing 1 and the second shaft portion 7 of the turbine 2. In this case, since air passes through the inside of the air blowoff grooves M1, M2 and M3, almost no air passes through the first and second ball bearings 8 and 10 having the shields 28, 29, 38 and 39, so that the possible scattering of the lubricant oil due to air in the first and second ball bearings 8 and 10 is prevented.

According to the second embodiment, dust and any foreign substance are prevented from entering from the outside through the gap between the lid 13 and the first shaft portion 6 of the turbine 2 while the impeller portion 5 is rotating at high speeds. Furthermore, dust and other foreign substances are prevented from entering from the outside through the gap between the housing 1 and the second shaft portion 7 of the turbine 2. Therefore, according to the second embodiment, dust and other foreign particles are prevented from entering the interior of the handpiece.

Figure 6:
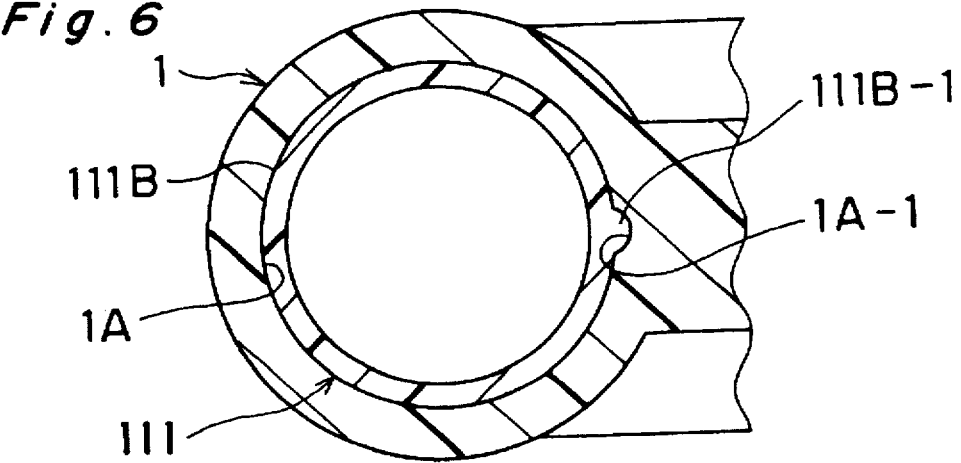
FIG. 6 is a sectional view taken along a line VI—VI shown in FIG. 5.
Figure 5:
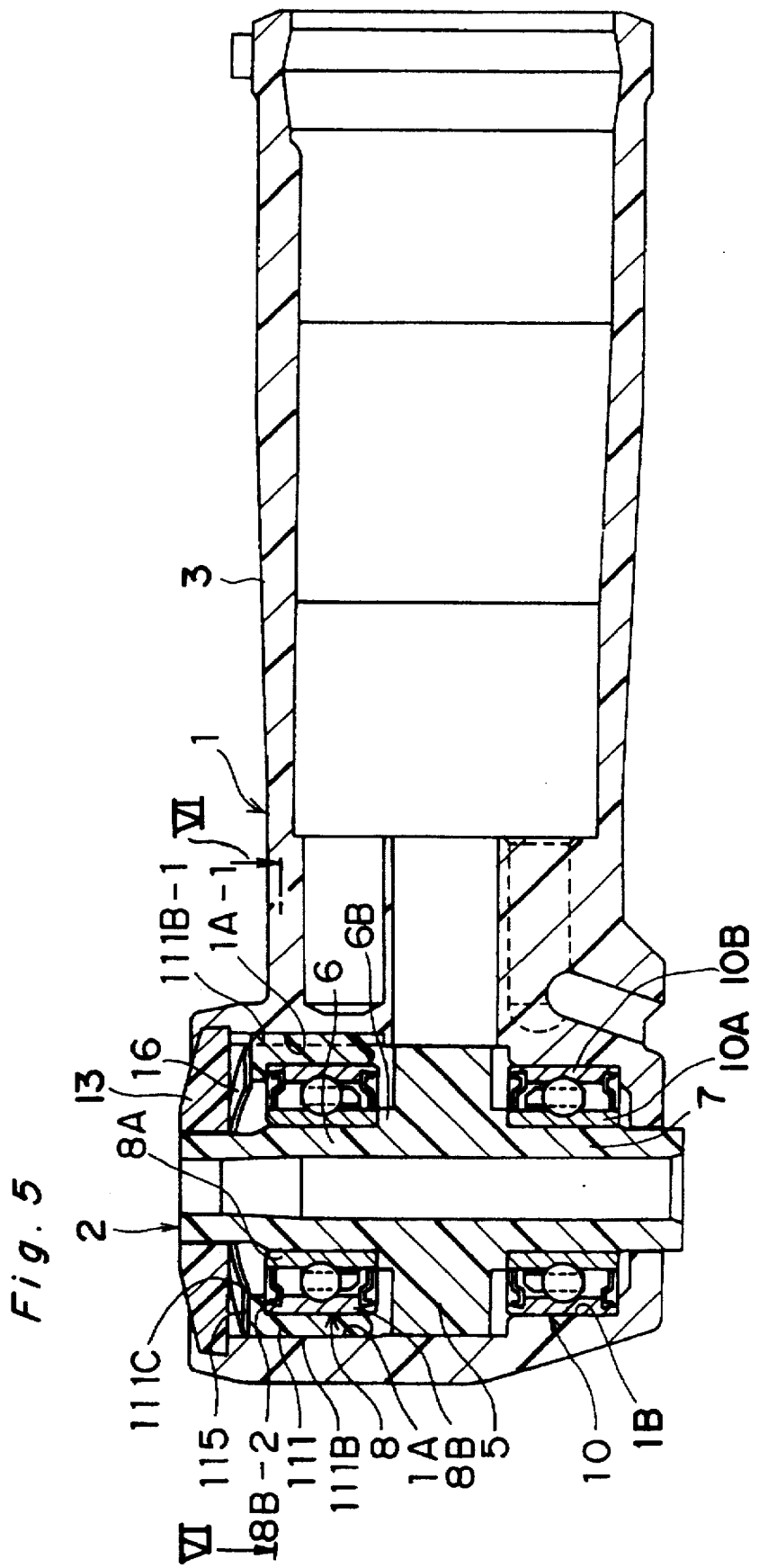
FIG. 5 is a sectional view of a dental handpiece according to a third embodiment of the present invention.
Figure 7:
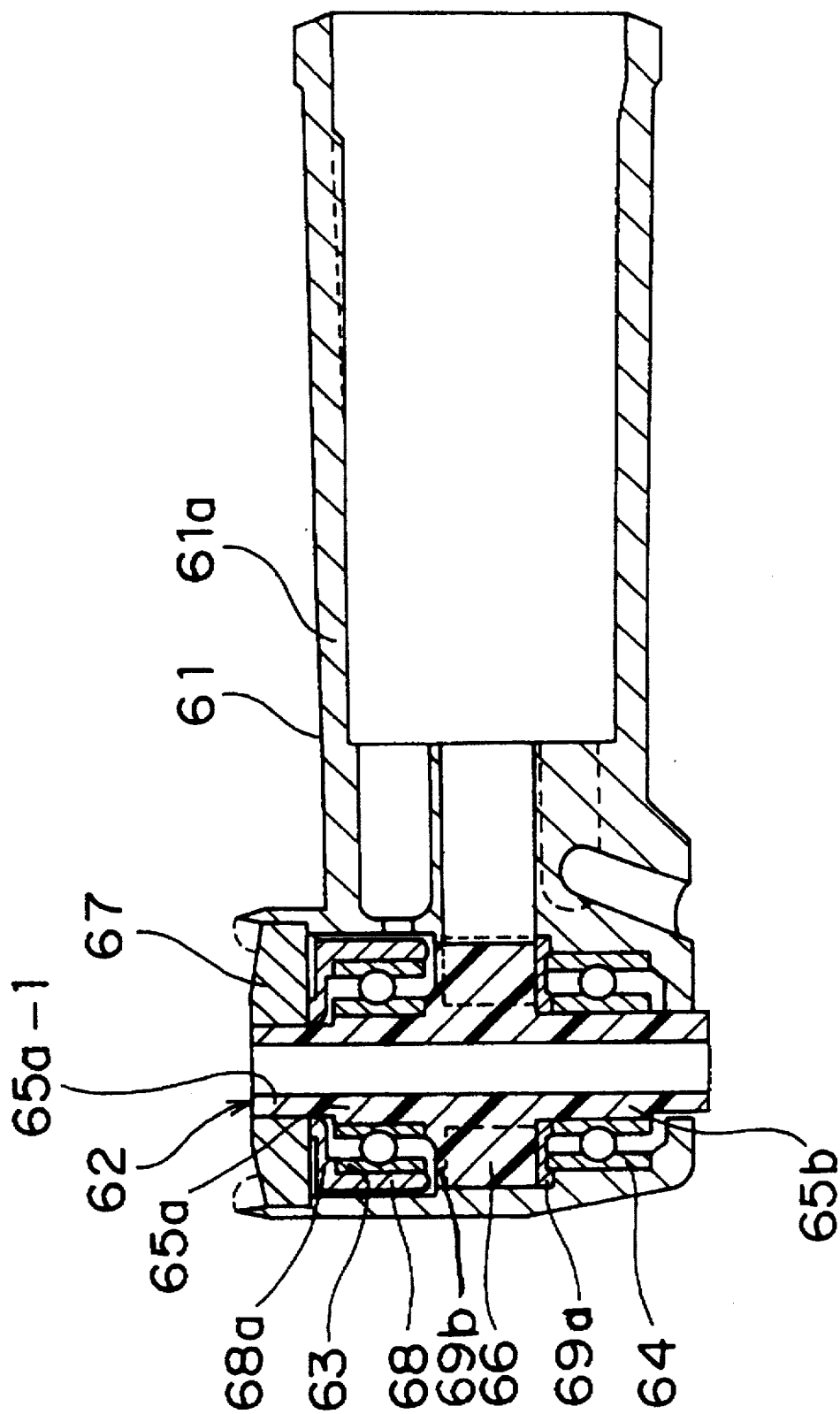
FIG. 7 is a sectional view of a prior art dental handpiece.

Next, FIGS. 5 and 6 show a dental handpiece according to a third embodiment of the present invention. The third embodiment differs from the first embodiment only in that a retainer 111 is provided in place of the retainer 11, and the inner circumferential surface of the housing 1 on a first ball bearing 8 side of the impeller portion 5 is modified. Therefore, the point different from the first embodiment will be described, and the same components as those of the first embodiment are denoted by the same reference numerals, with no detailed description provided therefor.

As shown in FIGS. 5 and 6, according to the retainer 111 of the third embodiment, an end surface 115, pressed axially by the conical spring washer 16, has a ring shape and a flat surface which is not formed with an axial projection. As shown in FIG. 6, the retainer 111 has a cylindrical outer circumferential surface 111B and is formed with a radially protruding approximately semi-circular convex portion 111B-1 which serves as an engagement portion. The convex portion 111B-1 extends axially.

On the other hand, the inner circumferential surface 1A of the housing 1 has a cylindrical shape to be fit on the outer, circumferential surface 111B of the retainer 111, and has a concave portion 1A-1 which serves as an engagement portion to be engaged with the convex portion 111B-1 of the retainer 111. The concave portion 1A-1 extends axially on the retainer.

The retainer 111 and the housing 1 of the third embodiment are engaged with each other by virtue of the convex portion 111B-1 and the concave portion 1A-1 which interfit with each other so as to be unable to rotate relative to each other, further, the retainer 111 and the housing 1 are fit to each other on their approximately cylindrical surfaces. Therefore, as shown in FIG. 5, the outer circumferential surface of the conical spring washer 16 can be tightly fit on the inner circumferential surface 1A of the housing 1. Therefore, according to the third embodiment, even when the retainer 111 has no projection for positioning the conical spring washer 16 in contrast to the first embodiment, the conical spring washer 16 does not deviate from the central axis of the turbine 2.

Therefore, according to the third embodiment, the conical spring washer 16 presses the end surface 115 of the retainer 111 with a force which is symmetrical about the central axis. Thus, an inner flange 111C of the retainer 111 presses the end surface 8B-2 of the outer ring 8B of the first ball bearing 8 with a force which is symmetrical about the central axis. Therefore, the inner ring 8A of the first ball bearing 8 axially presses the stepped portion 6B of the first shaft portion 6 with a force which is symmetrical about the central axis. Therefore, even when the turbine 2 rotates at high speeds, the turbine 2 is prevented from shaking along the axial direction. Therefore, the turbine 2 is always stably supported by the first and second ball bearings 8 and 10. That is to say, according to the third embodiment, even when the turbine 2 rotates at high speeds, the turbine 2 is always stably supported by the first and second ball bearings 8 and 10. Furthermore, similarly to the second embodiment, the third embodiment has grooves for discharging air on the inner circumferential surface of the housing 1, though the grooves are not shown.

The fitting surfaces of the retainer 11 and the housing 1 are each formed in an approximately regular octagonal shape in the first and second embodiments. However, it is of course acceptable to form the fitting surfaces in any polygonal shape. Furthermore, in the third embodiment, the convex portion 111B-1 is provided on the outer circumferential surface of the retainer 111, and the concave portion 1A-1 is provided on the inner circumferential surface of the housing 1. However, it is acceptable to provide a concave portion on the outer circumferential surface of the retainer and provide a convex portion on the inner circumferential surface of the housing. What is essential is that the retainer and the housing are required to have complimentary shapes which can be fitted to each other so as to prevent relative rotation.

Moreover, in the second embodiment, the air blowoff grooves are formed on the inner circumferential surface of the housing 1. However, it is acceptable to form an air blowoff groove on the outer circumferential surface of the outer ring of each ball bearing or form an air blowoff groove on the inner circumferential surface of the inner ring of each ball bearing.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A dental handpiece comprising:
   a synthetic resin housing having a shank portion, defining air inflow and outflow passageways, and a head portion, connected to said shank portion, defining a through hole extending between a first opening and a second opening;
   a synthetic resin turbine, supported in said head portion of said housing adjacent said shank portion, including a first shaft portion, a second shaft portion, and an impeller portion positioned between and integrally connected to said first and second shaft portions;
   a first ball bearing positioned between said first shaft portion and said housing, said first ball bearing having an inner ring and an outer ring, wherein said inner ring is fitted on said first shaft portion;
   a second ball bearing positioned between said second shaft portion and said housing, said second ball bearing having an inner ring and an outer ring, wherein said inner ring is fitted on said second shaft portion;
   a retainer fitted on said outer ring of said first ball bearing, said retainer having an outer peripheral surface which forms a polygon in cross section and an end surface, remote from said impeller, having an outer periphery in the shape of a polygon which defines a plurality of corner areas on said end surface of said retainer, said end surface including a plurality of projections located at said plurality of corner areas, respectively, wherein said outer peripheral surface of said retainer closely corresponds to an opposing inner peripheral surface of said housing which forms a polygon in cross section, such that relative rotation between said retainer and said housing is prevented, and said retainer is axially moveable with respect to said opposing inner peripheral surface of said housing;

a lid engaging said first opening and extending between said first opening and an end portion of said first shaft portion which is remote from said impeller; and a conical spring washer located between said lid and said retainer, said conical spring washer biasing said retainer toward said impeller, wherein said conical spring washer is radially supported by said projections.

2. The dental handpiece as claimed in claim 1, wherein each of said projections includes a surface which is inclined relative to said end surface such that each said projection extends further away from said upper surface as a radial distance from a center of said upper surface increases.

3. The dental handpiece as claimed in claim 1, wherein a groove is formed in at least one of an outer peripheral surface of said outer ring of said first ball bearing, an outer peripheral surface of said outer ring of said second ball bearing, an inner peripheral surface of said inner ring of said first ball bearing, an inner peripheral surface of said inner ring of said second ball bearing, said inner peripheral surface of said housing which opposes said outer peripheral surface of said retainer, and said inner peripheral surface of said housing which opposes said outer peripheral surface of said outer ring of said second ball bearing.

4. The dental handpiece as claimed in claim 1, wherein a first groove is formed in said inner peripheral surface of said housing which opposes said outer peripheral surface of said retainer, said groove establishing fluid communication between a space, between said first ball bearing and said impeller portion, and a space between said lid and said retainer.

5. The dental handpiece as claimed in claim 4, wherein:

a second groove is formed in an inner peripheral surface of said housing which opposes said outer peripheral surface of said outer ring of said second ball bearing; and a third groove, fluidly communicating with said second groove, is formed in an inner peripheral surface of said housing which opposes an end of said second ball bearing, such that said second and third grooves establish fluid communication between a space, between said second ball bearing and said impeller portion, and a space located axially outward of said second ball bearing.

* * * * *